(12) United States Patent
Nemoto et al.

(10) Patent No.: US 8,968,246 B2
(45) Date of Patent: Mar. 3, 2015

(54) SYRINGE ADAPTER

(75) Inventors: Shigeru Nemoto, Tokyo (JP); Takashi Saitoh, Tokyo (JP); Shigeru Muramatsu, Tokyo (JP); Hirofumi Uchizono, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 549 days.

(21) Appl. No.: 13/257,287

(22) PCT Filed: Mar. 17, 2010

(86) PCT No.: PCT/JP2010/054522
§ 371 (c)(1),
(2), (4) Date: Sep. 16, 2011

(87) PCT Pub. No.: WO2010/107054
PCT Pub. Date: Sep. 23, 2010

(65) Prior Publication Data
US 2012/0004543 A1  Jan. 5, 2012

(30) Foreign Application Priority Data

Mar. 18, 2009 (JP) ................................. 2009-065888
Aug. 20, 2009 (JP) ................................. 2009-191130

(51) Int. Cl.
*A61M 1/00* (2006.01)
*A61M 5/145* (2006.01)

(52) U.S. Cl.
CPC ....... *A61M 5/14546* (2013.01); *A61M 5/14566* (2013.01); *A61M 2205/14* (2013.01); *A61M 2205/6054* (2013.01)
USPC ...................................................... 604/152

(58) Field of Classification Search
CPC ................... A61M 5/14546; A61M 5/14566; A61M 5/3135; Y10S 128/01
USPC .......................................... 604/152; 600/432
See application file for complete search history.

(56) References Cited

U.S. PATENT DOCUMENTS

| 5,913,844 A | 6/1999 | Ziemba et al. |
| 7,081,104 B2 * | 7/2006 | Neer et al. .................. 604/152 |

(Continued)

FOREIGN PATENT DOCUMENTS

| CN | 1572334 A | 2/2005 |
| JP | 01-284266 | 11/1989 |

(Continued)

OTHER PUBLICATIONS

Office Action mailed on Dec. 10, 2013 in Japanese Patent Application No. 2011-504857.

(Continued)

*Primary Examiner* — Kevin C Sirmons
*Assistant Examiner* — Deanna K Hall
(74) *Attorney, Agent, or Firm* — Knobbe Martens Olson & Bear LLP

(57) ABSTRACT

Syringe adapter 300 has base member 310 and flange lock member 320. Flange lock member 320 is formed in generally arc shape as a whole so as to receive a cylinder flange inside. Flange lock member 320 has look hook 323 and engagement hook 324 formed thereon. Look hook 323 locks the cylinder flange by rotation of a syringe received in flange lock member 320 about its axis. Engagement hook 324 locks syringe adapter 300 to the apparatus so as not to release lock to the apparatus in the state in which the cylinder flange of the syringe is received in flange lock member 320.

11 Claims, 10 Drawing Sheets

(56) References Cited

U.S. PATENT DOCUMENTS

| | | |
|---|---|---|
| 2001/0021823 A1 | 9/2001 | Nemoto |
| 2004/0133161 A1 | 7/2004 | Trocki et al. |
| 2004/0249276 A1 | 12/2004 | Nemoto et al. |

FOREIGN PATENT DOCUMENTS

| | | |
|---|---|---|
| JP | A-2002-11096 | 1/2002 |
| JP | 2003-220136 A | 8/2003 |
| JP | 2004-154238 A | 6/2004 |
| JP | 2005-000203 A | 1/2005 |
| JP | A-2006-500087 | 1/2006 |
| JP | 2007-252481 A | 10/2007 |
| WO | WO 2004/012787 | 2/2004 |

OTHER PUBLICATIONS

Office Action issued on Feb. 20, 2013 in Chinese Patent Application No. 201080021840.6.

International Preliminary Report on Patentability dated Oct. 27, 2011 in corresponding Application No. PCT/JP2010/054522.

* cited by examiner

SYRINGE ADAPTER

CROSS-REFERENCE TO RELATED APPLICATIONS

This application is the U.S. National Phase under 35. U.S.C. §371 of International Application PCT/JP2010/054522, filed Mar. 17, 2010, which claims priority to Japanese Patent Application No. 2009-065888, filed Mar. 18, 2009 and Application No. 2009-191130, filed Aug. 20, 2009. The International Application was published under PCT Article 21(2) in a language other than English.

TECHNICAL FIELD

The present invention relates to a syringe adapter removably mounted on a chemical liquid injector for injecting a chemical liquid filled in a syringe into a patient in order to allow the chemical liquid injector to hold the syringe.

BACKGROUND ART

Currently employed medical imaging diagnostic apparatuses include CT (Computed Tomography) scanners, MRI (Magnetic Resonance Imaging) apparatuses, PET (Positron Emission Tomography) apparatuses, angiography apparatuses, MRA (MR Angiography) apparatuses and the like. For obtaining CT images of a patient with the abovementioned apparatuses, a chemical liquid such as a contrast medium or physiological saline is often injected into the patient's body.

In general, the injection of the chemical liquid into the patient is automatically performed by using a chemical liquid injector. The chemical liquid injector has an injection head on which a syringe filled with the chemical liquid is removably mounted and an injection control unit which controls the operation of the injection head. The syringe has a cylinder and a piston inserted thereinto to be movable in its axis direction. The chemical liquid is filled in the cylinder. The injection head includes a piston driving mechanism for pushing the piston of the syringe mounted on the injection head into the cylinder. After an injection needle is connected to the end of the cylinder through an extension tube and is inserted into a patient's blood vessel, the piston driving mechanism pushes the piston into the cylinder, so that the chemical liquid in the cylinder can be injected into the patient.

To inject the chemical liquid in the syringe reliably and safely in the abovementioned chemical liquid injector, it is important to allow the injection head to hold the syringe tightly. Patent Document 1 has disclosed a chemical liquid injector in which a pair of holding members is provided for holding a cylinder flange provided integrally with a cylinder of a syringe from both sides of the syringe on the left and right such that the holding member is held at a closed position for holding the syringe or at an opened position for allowing the insertion of the syringe depending on the mounting or demounting operation of the syringe.

There are a plurality of types of syringes having different diameters. To allow the mounting of such syringes having different diameters, adapters matching the diameters of syringes are used. In general, the adapter is removably mounted on the chemical liquid injector with a lock mechanism operated manually.

PRIOR ART REFERENCE

Patent Document

Patent Document 1: Japanese Patent Laid-Open No. 2004-154238

SUMMARY OF THE INVENTION

Problems to be Solved by the Invention

While the conventional chemical liquid injector described above has the advantage that the mounting and demounting of the syringe is extremely easy, the movement of the holding member from the closed position to the opened position is realized simply by pulling the syringe upward and thus the syringe may be removed unintentionally. In addition, while currently manufactured syringes have cylinder flanges of various shapes, for example depending on manufacturers or capacities, the abovementioned chemical liquid injector can hold only the syringes having cylinder flanges of a shape matching the holding member. Furthermore, when the syringe is mounted on the chemical liquid injector with the adapter interposed between them, the adapter should be mounted on the chemical liquid injector prior to the mounting of the syringe and this manual operation is burdensome.

It is an object of the present invention to provide a syringe adapter for allowing the mounting of syringes having cylinder flanges of various shapes on a chemical liquid injector, the syringe adapter enabling a syringe to be easily mounted thereon and demounted therefrom, easily mounted on and demounted from the chemical liquid injector, and capable of reliably holding the syringe mounted thereon without unintentional demounting.

Means for Solving the Problems

To achieve the abovementioned object, the present invention provides a syringe adapter for removably holding a syringe having a cylinder and a piston, the syringe adapter being mounted removably on an apparatus for operating the syringe, including a flange receiver, a flange lock mechanism, and an adapter lock mechanism. The flange receiver has a structure matching the shape of a cylinder flange formed at a trailing end of the cylinder of the syringe to be held so as to receive the cylinder flange. The flange lock mechanism locks the cylinder flange by rotation of the syringe received in the flange receiver about an axis of the cylinder. The adapter lock mechanism locks the syringe adapter to the apparatus so as not to release lock to the apparatus in the state in which the cylinder flange of the syringe is received in the flange receiver.

In the syringe adapter according to the present invention, preferably, the flange receiver has an arc-shaped portion having an inner circumferential surface with a radius of curvature substantially equal to a radius of curvature of an outer circumferential surface of the syringe flange, an arm portion extending from both ends of the arc-shaped portion and provided to be elastically displaceable with respect to the arc-shaped portion, and a grip portion formed on the arm portion, and part of an inner circumferential surface of the grip portion is formed on the extension of an arc shape of the inner circumferential surface of the arc-shaped portion, and the adapter lock mechanism is provided for on an outer surface of the arm portion. In this case, the adapter lock mechanism can have an engagement structure elastically engaging with an adapter receiving portion formed in the apparatus such that the syringe adapter is inserted therein.

The present invention also provides an apparatus on which the syringe adapter according to the present invention is removably mountable. The apparatus includes an adapter receiving portion into which the syringe adapter is inserted, and an engagement structure provided for the adapter receiving portion and locking the syringe adapter in cooperation with an adapter lock mechanism of the syringe adapter.

Effect of the Invention

According to the present invention, the syringes of various shapes can be mounted on the apparatus on which the syringe is removably mounted. In addition, the mounted syringe can be held tightly while the mounting and demounting of the syringe and the mounting and demounting on and from the apparatus are easily performed.

EMBODIMENT FOR CARRYING OUT THE INVENTION

Figure 1:
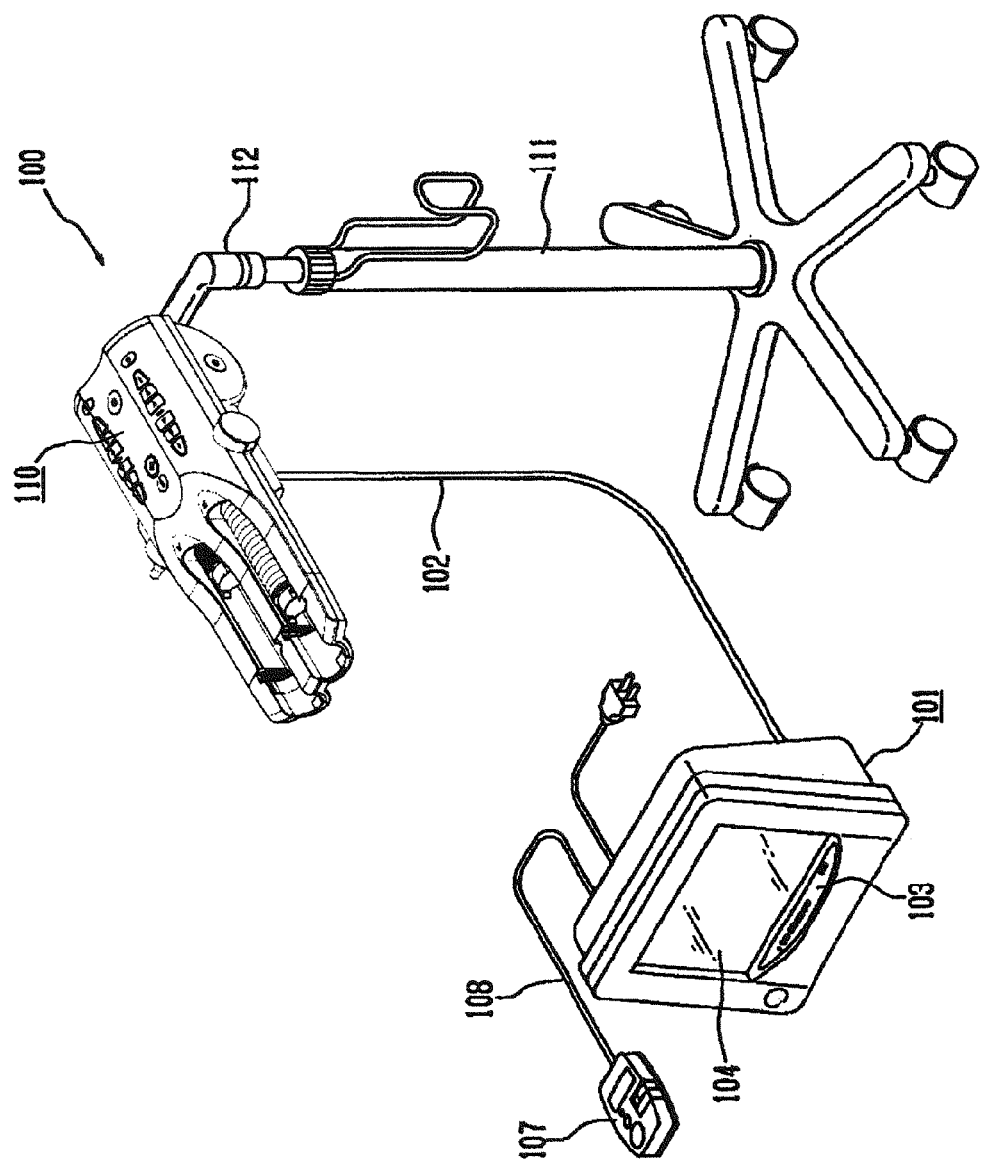
FIG. 1 A perspective view showing an example of a chemical liquid injector in which a syringe adapter according to the present invention is used.

Referring to FIG. 1, an example of chemical liquid injector 100 which employs a syringe adapter according to the present invention is shown. Chemical liquid injector 100 has injection head 110 and injection control unit 101 which controls the operation of injection head 110. Injection head 110 is attached to the top end of stand 111 by movable arm 112 and is connected to injection control unit 101 through cable 102. Injection control unit 101 has main operation panel 103, touch panel 104 serving as a display device and an input device, hand unit 107 connected thereto through cable 108 and serving as an auxiliary input device, and the like.

Figure 2:
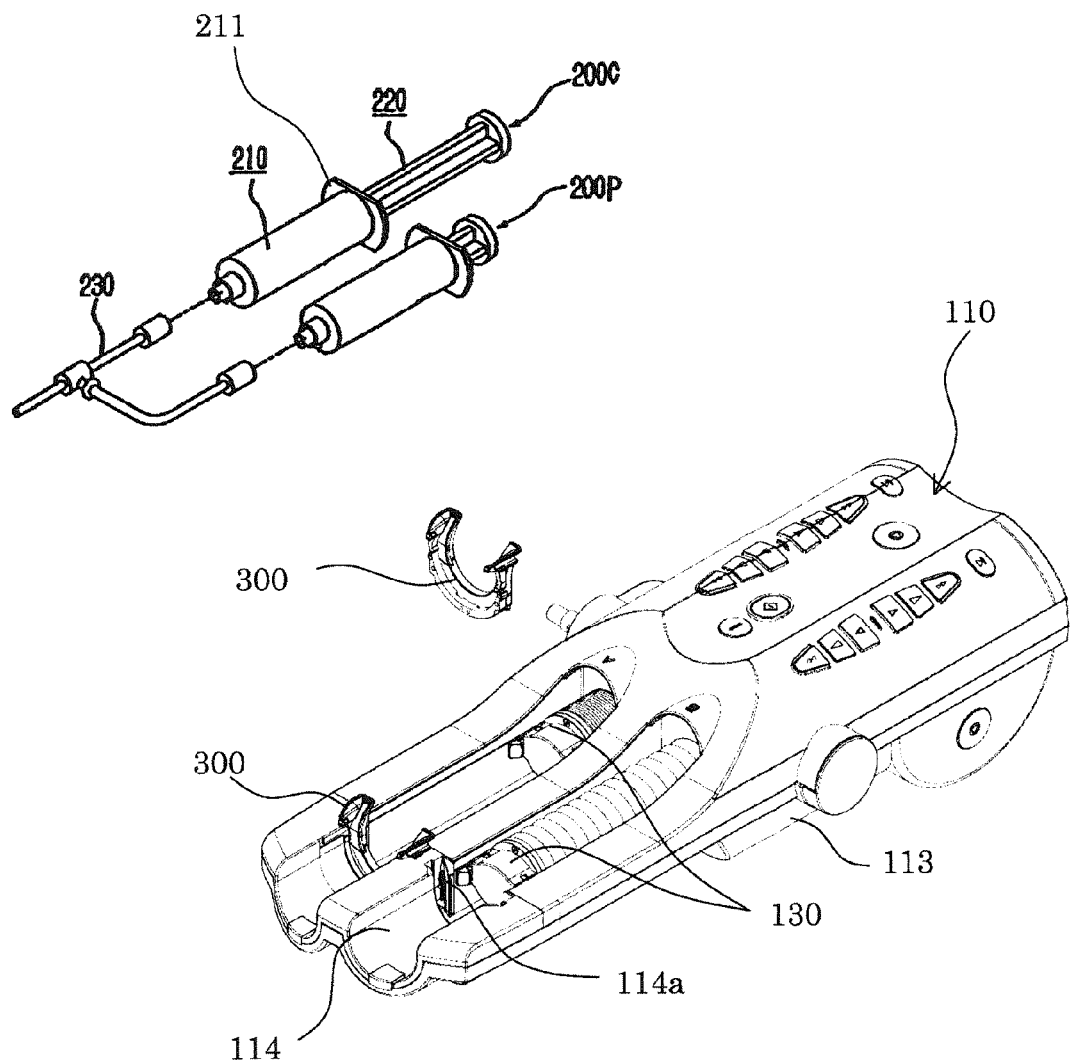
FIG. 2 A perspective view showing an injection head shown in FIG. 1 as well as a syringe and a syringe adapter to be mounted thereon.

As shown in FIG. 2, injection head 110 is provided for removably mounting two syringes 200C and 200P and has two concave portions 114 for supporting these syringes 200C and 200P in an upper surface of head body 113. Each of syringes 200C and 200P has cylinder 210 having cylinder flange 211 formed at its trailing end and piston 220 having a piston flange formed at its trailing end. Each of syringes 200C and 200P is filled with a chemical liquid. For example, one syringe 200C can be filled with a contrast medium and the other syringe 200P can be filled with physiological saline. Each of syringes 200C and 200P can be realized by using a syringe of a pre-filled type which is previously filled with a chemical liquid by a manufacturer, or a syringe of a field filling type which is filled with a chemical liquid as required in a medical location or the like. Connection tube 230 joining into one at an intermediate portion and provided with an injection needle at its leading end is connected to the leading ends of two syringes 200C and 200P mounted on head body 113.

Syringes 200C and 200P are mounted on injection head 110 with syringe adapter 300 interposed between them. Syringe adapter 300 is formed to hold the cylinder flanges of syringes 200C and 200P. In part of concave portion 114 of injection head 110, adapter receiver 114a serving as an adapter receiving portion provided to receive syringe adapter 300 is formed to have an opening in an upper portion. Syringe adapter 300 will be described later in detail.

Two piston driving mechanisms 130 which are independently driven for operating pistons 220 of mounted syringes 200C and 200P are provided for injection head 110 corresponding to the respective concave portions 114. Piston driving mechanisms 130 operate pistons 220 of mounted syringes 200C and 200P to allow the injection of the contrast medium and the physiological saline filled in syringes 200C and 200P separately or simultaneously into a patient. Piston driving mechanism 130 can be realized by employing a known mechanism used typically for the injector of this type.

Chemical liquid injector 100 is connected to an imaging diagnostic apparatus (not shown) for obtaining diagnostic images of a patient, for example an X-ray CT apparatus. After chemical liquid injector 100 injects the chemical liquid upon the injection conditions specified for the site of imaging, the body conditions of the patient or the like, the diagnostic imaging apparatus can obtain the diagnostic images of the patient.

Next, syringe adapter 300 mentioned above will be described in detail with reference to FIGS. 3 to 5. In the following description, syringes 200C and 200P held by syringe adapter 300 are not identified separately and the simple designation of "syringe 200" is used.

Cylinder adapter 300 has base member 310 and flange lock member 320 fixed to base member 310 for locking cylinder flange 211. While base member 310 and flange lock member 320 are formed of different members in the present embodiment, they may be formed integrally as one part.

Base member 310 has an inner circumferential surface formed in generally arc shape. The radius of curvature of the inner circumferential surface is set to be smaller than the radius of curvature of an outer circumferential surface of cylinder flange 211 and to avoid interference with piston 220 of syringe 200 when piston 220 is operated.

Flange lock member 320 has arc-shaped portion 321 having an inner circumferential surface formed in generally arc shape and is placed over base member 310 such that the radius of curvature of the inner edge is located coaxially with the radius of curvature of the inner edge of base member 310. While arc-shaped portion 321 is formed entirely in arc shape in the present embodiment, the outer surface of arc-shaped portion 321 may have an arbitrary shape as long as at least the inner circumferential surface is formed in arc shape.

Flange lock member 320 further has a pair of arm portions 322 extending in parallel with each other from both ends of arc-shaped portion 321 to form a U shape as a whole. Arm portions 322 are supported to be elastically displaceable with respect to arc-shaped portion 321 so that the interval between arm portions 322 can be changed. Thus, the fixing of base member 310 to flange lock member 320 is performed at arc-shaped portion 321.

Inner circumferential surface 321a of arc-shaped portion 321 has the radius of curvature substantially equal to the radius of curvature of the outer circumferential surface of cylinder flange 211 so that the outer circumferential surface of cylinder flange 211 is supported on inner circumferential surface 321a. The radius of curvature of inner circumferential surface 311 of base member 310 and the radius of curvature of inner circumferential surface 321a of flange lock member 320 are defined in this manner in association with the shape of cylinder flange 211 of cylinder 210 to result in a difference in height formed between base member 310 and arc-shaped portion 321 of flange lock member 320. The surface of base member 310 provided by this difference in height serves as flange receiving surface 330 for receiving the rear surface of cylinder flange 211.

Grip portion 325 is formed at the leading end of each arm portion 322 for manipulation by a user when flange adapter 300 is mounted or demounted. Part of an inward surface of grip portion 325 is located on the extension of the arc shape of inner circumferential surface 321a of arc-shaped portion 321. Thus, flange lock member 320 has the shape for receiving cylinder flange 211 on the inner side as a whole and provides a flange receiver matching the shape of cylinder flange 211 for removably receiving part of cylinder flange 211 together with flange receiving surface 330. A pair of arm portions 322 are located on both sides of the left and right of cylinder flange 211 received by this flange receiver.

Next, description will be made of cylinder flange 211 of syringe 200 held by syringe adapter 300.

Figure 6:
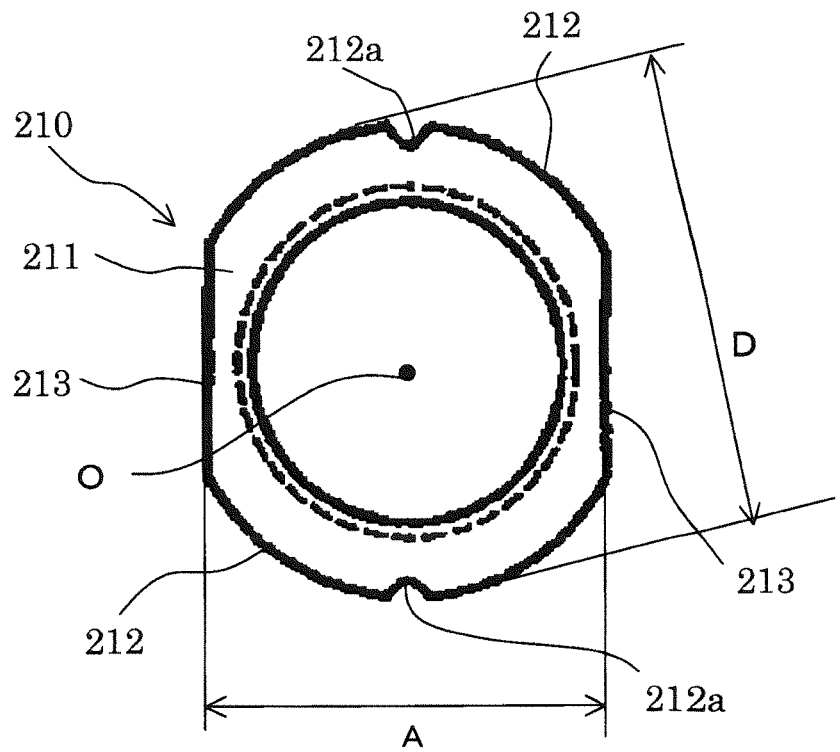
FIG. 6 A diagram showing a cylinder of the syringe shown in FIG. 2 viewed from the side of a cylinder flange.

As shown in FIG. 6, cylinder flange 211 formed at the trailing end of cylinder 210 is basically formed to have diameter D, but its opposite portions are cut in parallel. Thus, the outer circumferential edge of cylinder flange 211 is shaped to have two cut portions 213 formed at the opposite positions and arc-shaped portions 212 connecting the cut portions 213. Distance A between cut portions 213 is smaller than diameter D of arc-shaped portion 212. Two concave portions 212a are formed on the outer circumferential surface of arc-shaped portion 212 at the positions rotated 90 degrees with respect to cut portions 213 to be symmetric about center O of cylinder flange 211.

Referring again to FIG. 3 and FIG. 4, each arm portion 322 of flange lock member 320 has lock hook 323 as a flange lock mechanism. Lock hook 323 extends from grip portion 325 toward arc-shaped portion 321 and is supported on grip portion 325 such that look hook 323 is elastically displaced outward. Protruding portion 323a protruding inward is formed at the end of each lock hook 323. Protruding portion 323a is formed to have dimensions engaging with concave portion 212a of cylinder flange 211 shown in FIG. 6. The distance between two protruding portions 323a is greater than distance A between cut portions 213 of cylinder flange 211 and to be smaller than diameter D of arc-shaped portion 212.

Figure 7A:
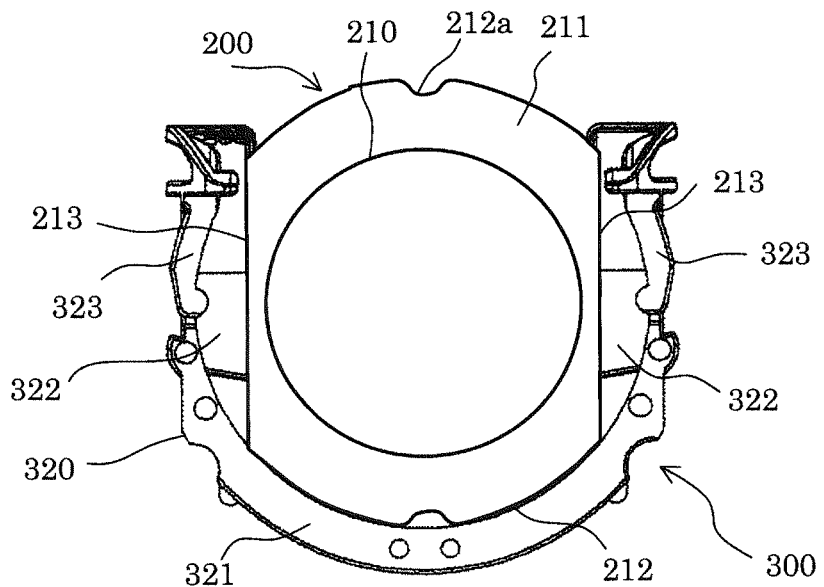
FIG. 7A A diagram for explaining how to mount the syringe on the syringe adapter, showing the syringe inserted in the syringe adapter.
Figure 7B:
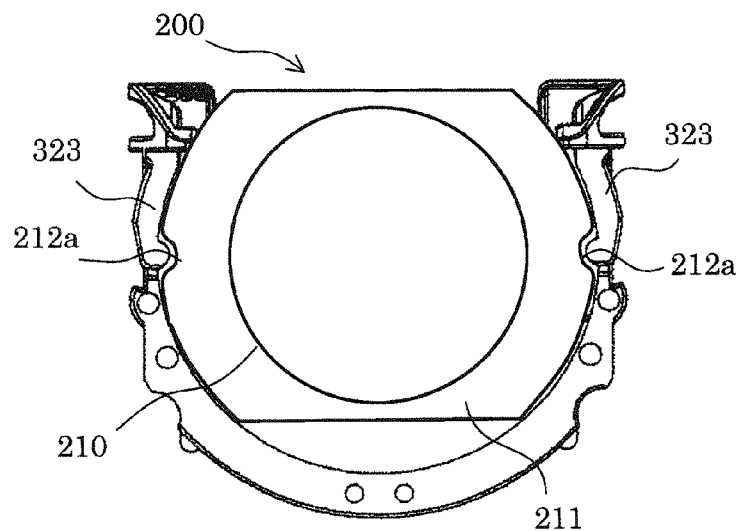
FIG. 7B A diagram for explaining how to mount the syringe on the syringe adapter, showing the syringe held by the syringe adapter.

As shown in FIG. 7A, when syringe 200 is inserted into syringe adapter 300 in the orientation in which cut portions 213 of cylinder flange 211 are opposite to lock hooks 323, syringe 200 can be inserted into syringe adapter 300 without interference with lock hooks 323 until arc-shaped portion 212 of cylinder flange 211 abuts on arc-shaped portion 321 of flange lock member 320. In this state, when cylinder 200 is rotated 90 degrees about its axis, arc-shaped portion 212 of cylinder flange 211 abuts on lock hook 323 to displace elastically lock hook 323 outward, and finally, as shown in FIG. 7B, the protruding potion of lock hook 323 engages with concave portion 212a of cylinder flange 211 to lock syringe 200 elastically.

The force applied to lock syringe 200 by lock hook 323 is preferably set such that syringe 200 is not rotated in the subsequent connection of extension tube 230 to syringe 200 (see FIG. 2) and the like but can be rotated by an adequate force when the user attempts to rotate syringe 200 in order to release the engagement of lock hook 323 and concave portion 212a.

Figure 8:
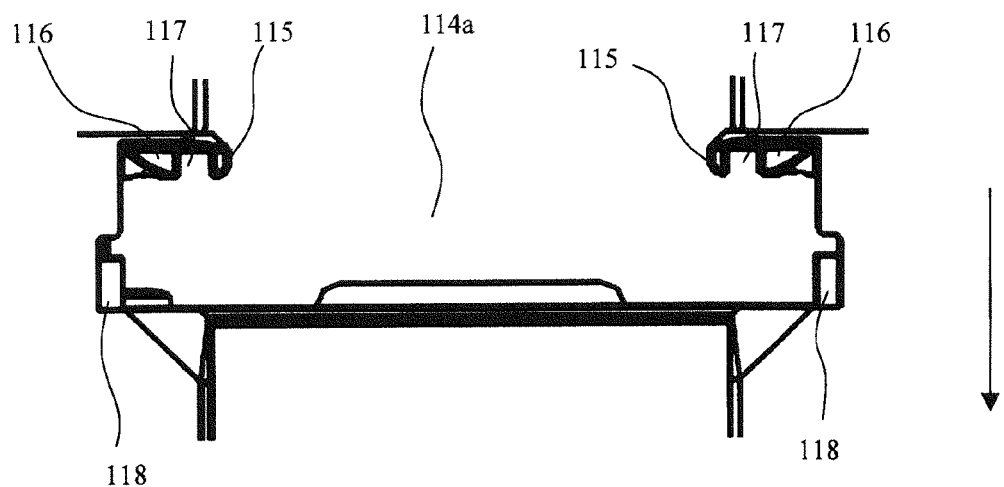
FIG. 8 A plan view near an adapter receiver of a head body shown in FIG. 2.
Figure 9:
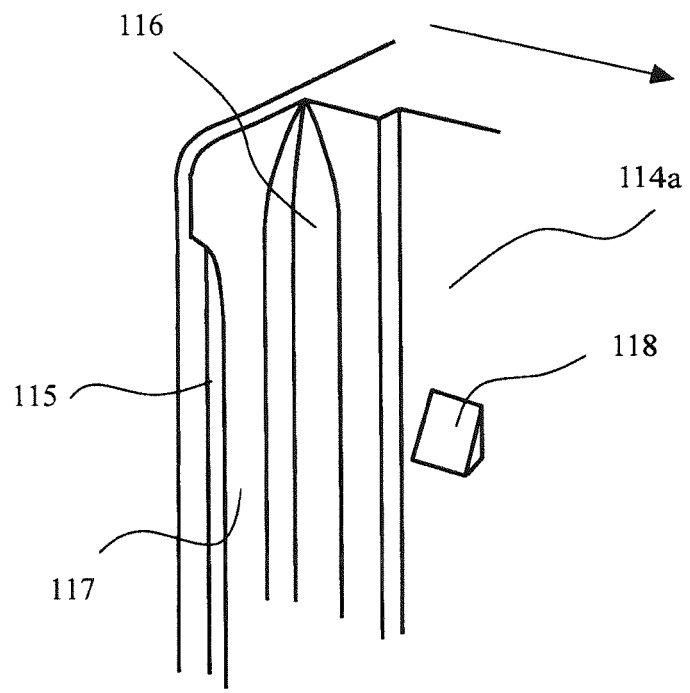
FIG. 9 A perspective view showing the adapter receiver shown in FIG. 2 viewed from the side of a piston driving mechanism.

As described above, syringe adapter 300 is mounted on adapter receiver 114a of injection head 110 (see FIG. 2). Adapter receiver 114a is formed as a concave portion for inserting cylinder adapter 300 and has guide grooves 117 on both sides for guiding the insertion of cylinder adapter 300 as shown in FIG. 8 and FIG. 9. Each of guide grooves 117 is formed to extend in the insertion direction of syringe adapter 300 (see FIG. 3) between two ribs 115 and 116 formed in the inner surface of adapter receiver 114a to extend in the insertion direction of syringe adapter 300. In FIG. 8 and FIG. 9, the direction indicated by each arrow represents the leading end of the syringe.

Figure 5:
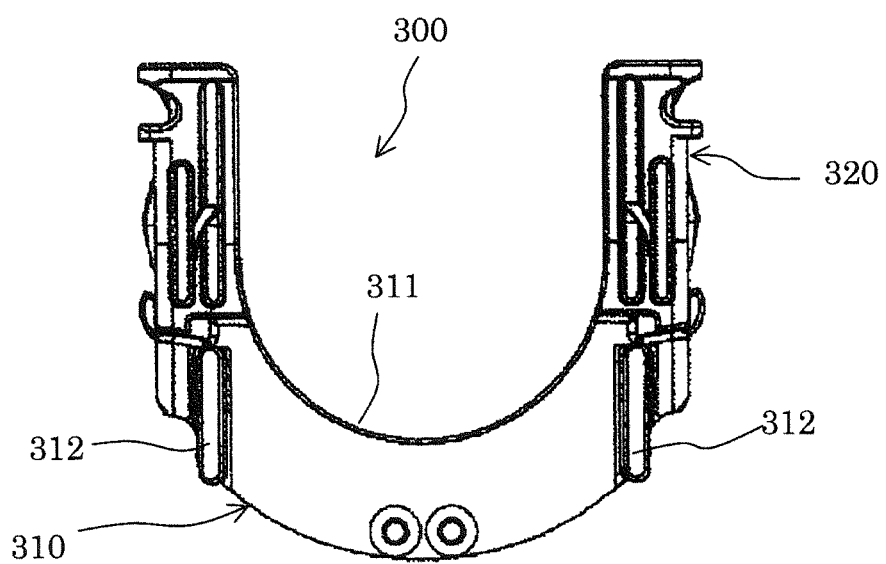
FIG. 5 A back view of the syringe adapter shown in FIG. 2.

On the other hand, as shown in FIG. 5, base member 310 of syringe adapter 300 has ribs 312 formed on both sides in the width direction of base member 310 for insertion into the abovementioned guide grooves 117.

Figure 3:
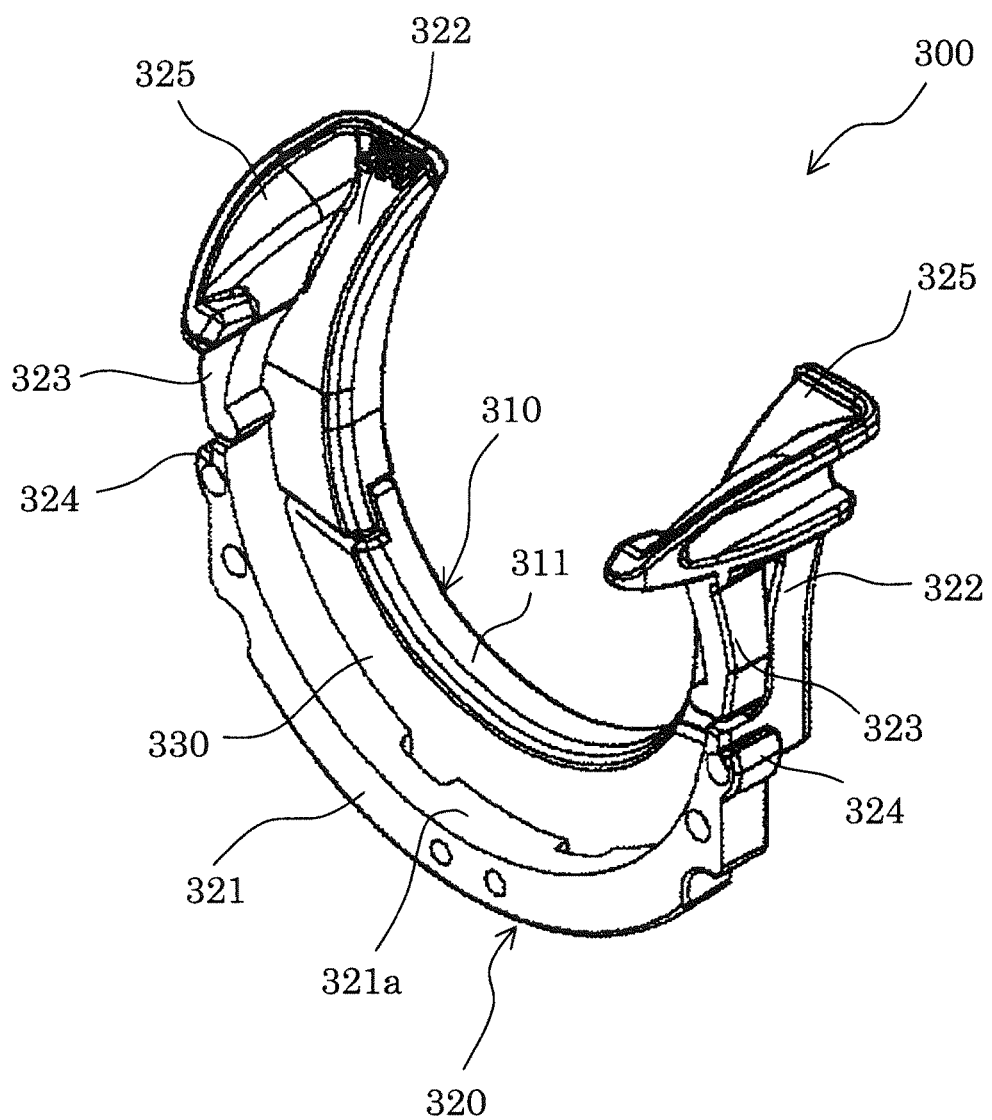
FIG. 3 A perspective view showing the syringe adapter shown in FIG. 2 viewed from a front side.
Figure 4:
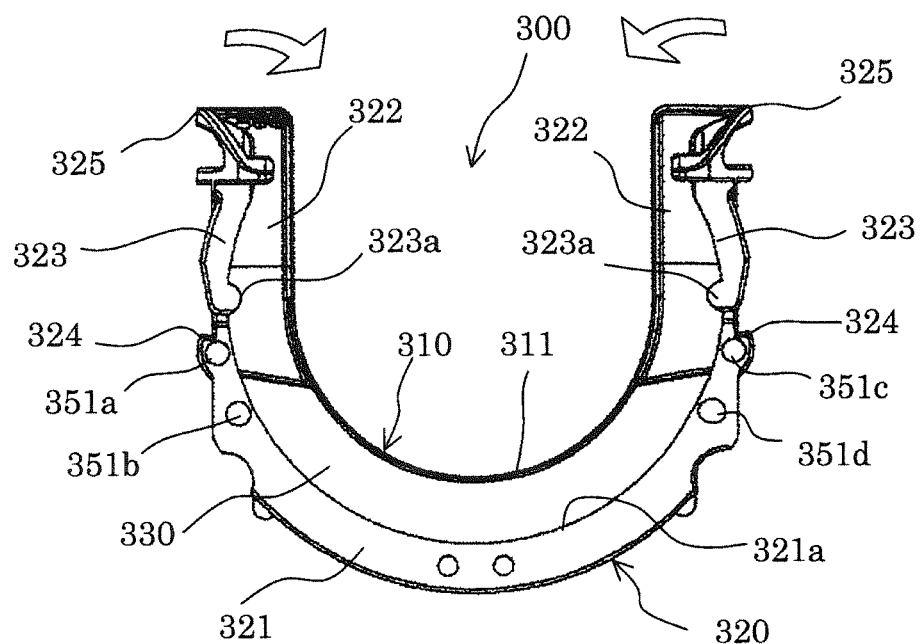
FIG. 4 A front view of the syringe adapter shown in FIG. 2.

In addition, as shown in FIG. 3 and FIG. 4, each of arm portions 322 of flange lock member 320 has engagement hook 324 serving as an adapter lock mechanism formed on the outer surface. In association therewith, as shown in FIG. 8 and FIG. 9, adapter receiver 114a has engagement hook 118 serving as an engagement structure for locking syringe adapter 300 in cooperation with the adapter lock mechanism. Engagement hook 324 and engagement hook 118 are formed to have the position relationship and the shapes to engage with each other when syringe adapter 300 is inserted to a predetermined position in adapter receiver 114a.

The engagement and the disengagement of engagement hook 324 of syringe adapter 300 and engagement hook 118 of adapter receiver 114a are achieved since at least the portions of flange lock member 320 that have engagement hooks 324 formed thereon are supported to be elastically displaceable inward, preferably arm portions 322 of syringe adapter 300 are supported to be elastically displaceable inward (see open arrows in FIG. 4).

For realizing the elastic displacement, in the present embodiment, the entire flange lock member 320 is formed of a material having elasticity to the extent that engagement hook 324 is elastically deformed to engage with engagement hook 118 of adapter receiver 114a. Example of the material having such elasticity include polyamide, polycarbonate, polyacetal, resin material such as ABS, and metal material such as phosphor bronze. Since the formation of the entire flange lock member 320 of the elastic material can simultaneously achieve the elastic displacement function of lock hook 323 described above, flange lock member 320 can be constructed of one part, and the structure of flange lock member 320 is simplified.

Alternatively, when engagement hook 324 is formed in arm portion 322 as in the present embodiment, only arm portion 322 of flange lock member 320 may be made of an elastic material. Alternatively, arm portion 322 may be formed as a separate part which is elastically urged by a spring or the like toward the other portions, and in this case, the materials of the parts are not limited particularly.

In any case, when the user attempts to take syringe adapter 300 inserted in adapter receiver 114a out of adapter receiver 114a, the user holds grip portions 325 on both sides to displace arm portions 322 inward to release the engagement of engagement hook 324 and engagement hook 118. At this point, when arm portions 322 are displaced more than necessary, flange lock member 320 may be broken. To avoid this, in the present embodiment, as shown in an enlarged view in FIG. 10, abutting surfaces 313 and 327 oppositely placed at an interval between them are formed as a stopper structure on base member 310 and flange lock member 320, respectively, in order to limit the inward displacement amount of arm portions 322. When arm portions 322 are displaced inward (to the left in FIG. 10), abutting surfaces 313 and 327 abut on each other, and arm portions 322 are not displaced further. This prevents any breakage of arm portions 322 due to extreme displacement.

Arm portion 322 also has inclined rib 326 formed at the position located on the extension of rib 312 formed on base member 310 and corresponding to the top end of guide groove 117 when cylinder flange 300 is inserted into adapter receiver 114a. Inclined rib 326 is formed such that its end less close to rib 312 is inclined toward inner rib 115 of ribs 115 and 117 shown in FIG. 8, and when arm portions 322 are displaced inward with cylinder adapter 300 inserted in adapter receiver 114a, the inside surface of inclined rib 326 abuts on the top end of rib 115.

Figure 10:
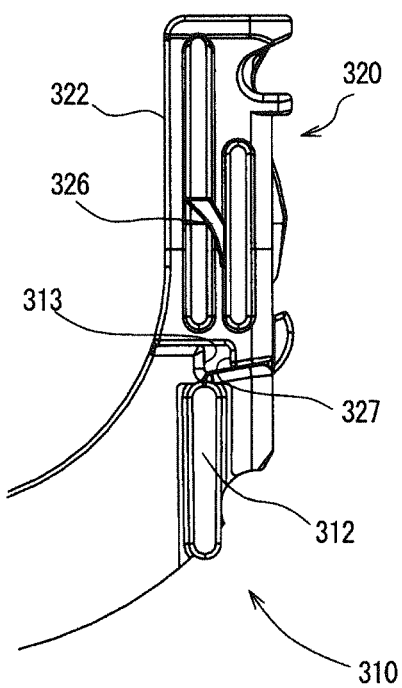
FIG. 10 An enlarged view showing one of arm portions of the syringe adapter shown in FIG. 2 viewed from the front side.

While FIG. 10 shows only one of arm portions 322, the other arm 322 is constructed in the same manner.

Next, description will be made of the mounting and demounting operation of syringe 200 on and from injection head 110 with syringe adapter 300 described above.

The user first holds grip portions 325 on both sides of syringe adapter 300 and mounts syringe adapter 300 on adapter receiver 114a of injection head 110. The mounting of syringe adapter 300 on adapter receiver 114a is performed by the engagement of engagement hooks 118 formed on adapter receiver 114a and engagement hooks 324 formed on arm portions 322 resulting from the inward elastic displacement of arm portions 322. This engagement causes syringe adapter 300 to be locked within adapter receiver 114a. Thus, syringe adapter 300 can be mounted with extreme ease only by inserting syringe adapter 300 into adapter receiver 114a until the engagement is achieved.

Syringe adapter 300 has rib 312 formed thereon. Since rib 312 is guided into guide groove 117 formed in adapter receiver 114a, the insertion into adapter receiver 114a can be performed smoothly. In addition, with rib 312 formed on syringe adapter 300, when syringe adapter 300 is in an opposite orientation, rib 312 serves as an obstacle and syringe adapter 300 cannot be inserted into adapter receiver 114a. This prevents the mounting of syringe adapter 300 in an erroneous orientation.

After syringe adapter 300 is mounted, the user mounts syringe 200 on syringe adapter 300. The mounting of syringe 200 can be performed as follows.

First, as shown in FIG. 7A, the user inserts syringe 200 between arm portions 322 of syringe adapter 300 until arc-shaped portion 212 of cylinder flange 211 abuts on arc-shaped portion 321 of flange lock member 320. At this point, syringe 200 is inserted in the orientation where cut portions 213 of cylinder flange 211 are opposite to lock hooks 323, thereby inserting syringe 200 smoothly. Since syringe adapter 300 is formed in U shape as a whole and has the wide opening between arm portions 322 into which syringe 200 is inserted, syringe 200 is easily inserted.

After syringe 200 is inserted, the user rotates syringe 200 about its axis. At this point, the outer circumferential surface of cylinder 210 is supported in concave portion 114 of injection head 110, and arc-shaped portion 212 of cylinder flange 211 and arc-shaped portion 321 of flange lock member 320 having substantially the same radius of curvature abut on each other, so that syringe 200 is rotated smoothly with the rotation center position maintained.

When syringe 200 is rotated to locate arc-shaped portion 212 of cylinder flange 211 at the position opposite to lock hook 323, lock hook 323 is pushed by arc-shaped portion 212 and is elastically displaced outward. When syringe 200 is further rotated and concave portion 212a of cylinder flange 211 reaches the position opposite to the protruding portion at the end of lock hook 323 as shown in FIG. 7B, lock hook 323 returns and engages with concave portion 212a of cylinder flange 211. This locks and holds syringe 200 in syringe adapter 300. The lock of syringe 200 is achieved by the engagement of lock hook 323 and concave portion 212a, and the click feel at the time of the engagement allows the user to recognize the lock of syringe 200 reliably, for example even when injection head 110 is located at a high position and the user cannot check visually the lock of syringe 200.

Figure 11:
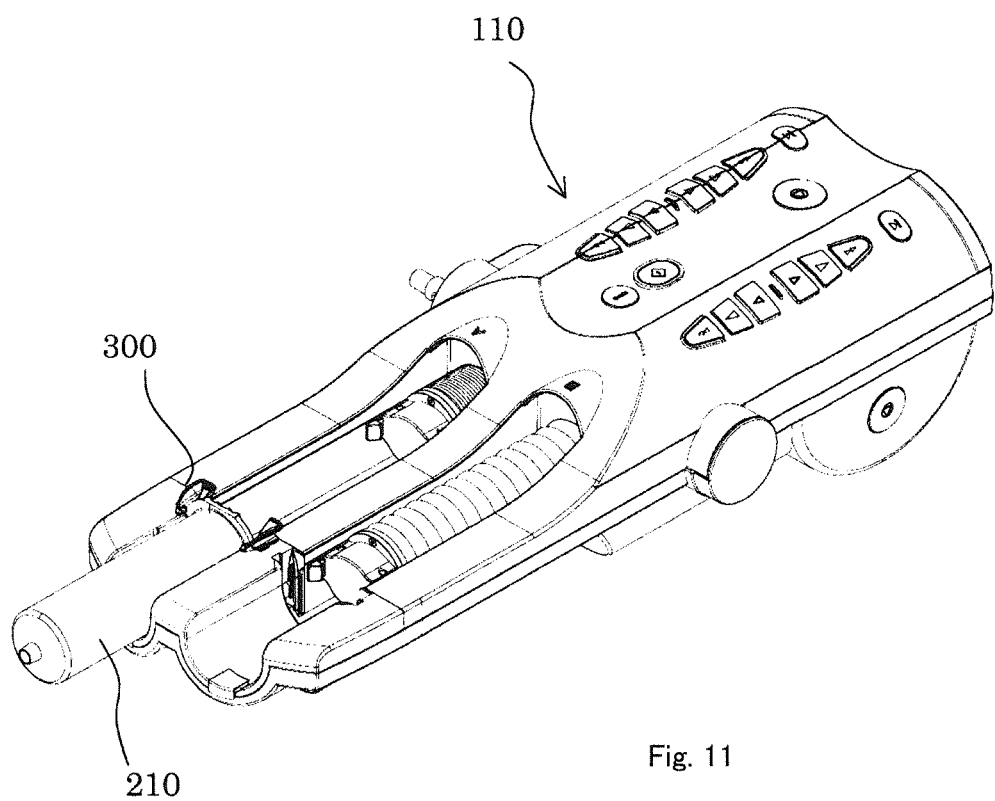
FIG. 11 A perspective view showing the mounted cylinder with the syringe adapter interposed.

FIG. 11 shows the state in which cylinder 210 is mounted on injection head 110 with syringe adapter 300 interposed between them.

Once syringe 200 is held in this manner, the mounting of syringe 200 on injection head 110 is completed. Then, the user connects connection tube 230 to the leading end of syringe 200 and operates chemical liquid injector 100 as appropriate to allow the injection of the chemical liquid filled in syringe 200 into the patient.

The demounting of syringe 200 from syringe adapter 300 may be performed by reversing the series of operations described above. Specifically, the user rotates syringe 200 to release the engagement of lock hook 323 and cylinder flange 211, and in this state, the user pulls up syringe 200 out of syringe adapter 300.

As described above, according to syringe adapter 300 of the present embodiment, the mounting and demounting of syringe 200 can be performed with extreme ease. In addition, since the mounting and demounting of syringe 200 involves the rotation operation of syringe 200, unintentional removal of syringe 200 can be prevented.

For removing syringe adapter 300 mounted on injection head 110, the user manipulates grip portions 325 of syringe adapter 300. Specifically, the user holds grip portions 325 on both side of syringe adapter 300 to displace arm portions 322 inward (in the direction in which they move closer to each other). This causes engagement hook 324 to be removed from engagement hook 118 of adapter receiver 114a. In this state, the user pulls out syringe adapter 300 in the direction in which syringe adapter 300 is removed from adapter receiver 114a, so that the user can remove syringe adapter 300.

As described above, inclined rib 326 is formed on arm portion 322, and when arm portion 322 is displaced inward, inclined rib 326 abuts on the top end of rib 115 formed on adapter receiver 114a. At this point, the force applied to inclined rib 326 by rib 115 causes cylinder adapter 300 to receive the force in an upward direction in FIG. 10, that is, in the direction in which syringe adapter 300 is removed from adapter receiver 114. Consequently, when arm portion 322 is displaced inward, syringe adapter 300 is raised from adapter receiver 114a to facilitate the removal of syringe adapter 300.

As described above, part of the inward surface of grip portion 325 provided for arm portion 322 is located on the extension of the arc shape of arc-shaped portion 321 having the radius of curvature corresponding to the diameter of cylinder flange 211. Thus, in the state in which cylinder flange 211 is received inside flange lock member 320, part of the inward surface of grip portion 325 interferes with the outer circumferential surface of cylinder flange 211, so that arm portion 322 cannot be displaced inward (in the direction in which they move closer to each other) until the engagement of engagement hook 324 and engagement hook 118 is released. As a result, in the state in which syringe 200 is held in syringe adapter 300, syringe adapter 300 cannot be removed from adapter receiver 114a, and this also prevents unintentional removal of syringe 200 mounted on injection head 110.

Figure 12:
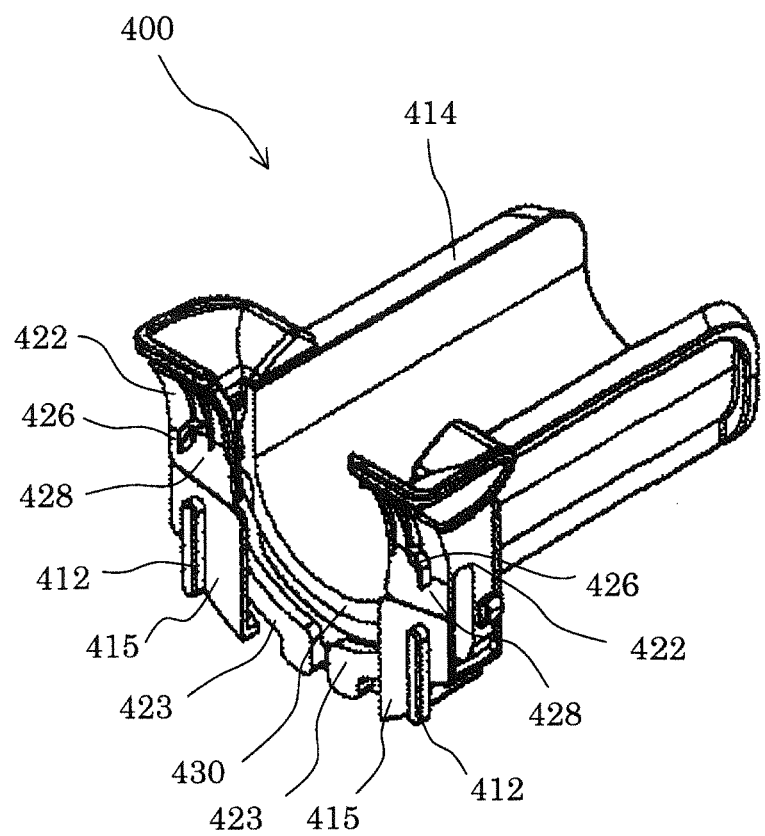
FIG. 12 A perspective view showing another embodiment of the syringe adapter according to the present invention viewed from the back side.
Figure 13:
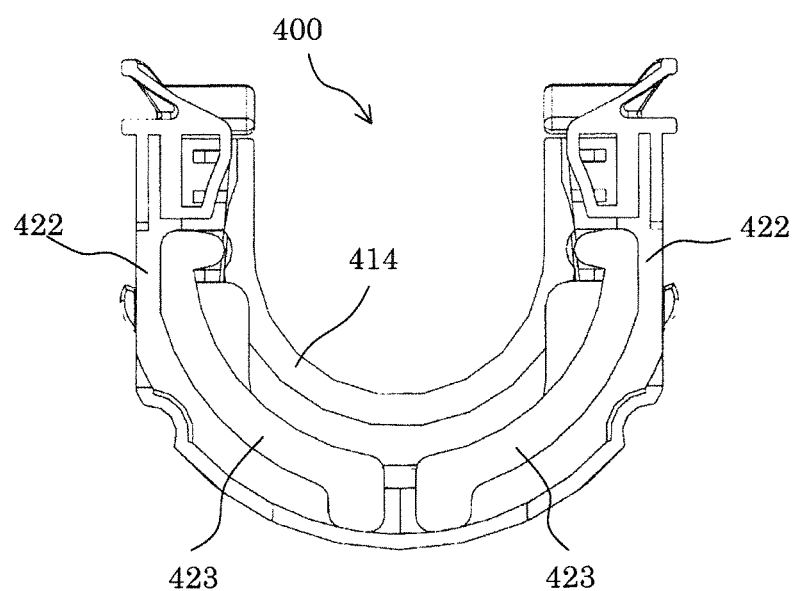
FIG. 13 A back view showing the syringe adapter shown in FIG. 12 while wall surfaces formed on a base member and a flange lock member are removed.

FIG. 12 and FIG. 13 show syringe adapter 400 according to another embodiment of the present invention.

Syringe adapter 400 shown in FIG. 12 and FIG. 13 also has a base member and a flange lock member which may be formed integrally, as in the embodiment described above, and can be mounted removably on adapter receiver 114a of injection head 110 shown in FIG. 2. Thus, the structure associated with adapter receiver 114a for mounting is the same as that in the embodiment described above. In the following, the same characteristics of syringe adapter 400 according to the present embodiment as those in the embodiment described above are omitted and only the different characteristics will be described.

Syringe adapter 400 according to the present embodiment holds a syringe (not shown) having a smaller diameter than that of syringe 200 held by syringe adapter 300 described above. When the syringe having the smaller diameter is mounted on injection head 110, a cylinder of the syringe is raised from concave portion 114 of injection head 110. To address this, in the present embodiment, cylinder support portion 414 for supporting the cylinder is formed integrally with the base member. Cylinder support portion 414 is formed in generally semicylindrical shape extending on concave portion 114 of injection head 110 when cylinder support portion 414 is mounted on injection head 110. The radius of the inner circumferential surface of cylinder support portion 414 is substantially equal to the radius of the outer circumferential surface of the cylinder to be held. This enables the stable support of the syringe having the smaller diameter on injection head 110.

Two plate-shaped portions 415 opposite to flange receiving surface 430 at an interval between them are formed on the base member on both sides in the width direction of the base member. The interval between flange receiving surface 430 and plate-shaped portion 415 is larger than the thickness of the cylinder flange, and the cylinder flange can be held between flange receiving surface 430 and plate-shaped portion 415. With plate-shaped portion 415 formed on the base member, rib 412 serving as a guide in mounting syringe adapter 400 on the injection head is formed on the outer wall surface of plate-shaped portion 415.

In correspondence with plate-shaped portion 415, two plate-shaped portions 428 opposite to flange receiving surface 430 at an interval between them are also formed on the flange lock member on both sides in the width direction of the flange lock member. In association therewith, inclined rib 426 is formed on the outer wall surface of plate-shaped portion 428.

These plate-shaped portions 415 and 428 are formed to have the function as a stopper which prevents extreme displacement of arm portions 422 by the abutment of the end faces of the plate-shaped portions when arm portions 422 are to be displaced extremely.

Lock hook 423 serving as a flange lock mechanism is supported to be elastically displaceable on an arc-shaped portion and extends therefrom toward arm portion 422 along the arc-shaped portion. In this manner, the form of the flange lock mechanism is different from the flange lock mechanism of syringe adapter 300, but the function and the mounting/demounting operation of the syringe are similarly performed. It should be noted that the flange lock mechanism according to the present embodiment can be applied to the flange lock mechanism of syringe adapter 300 described above, and vice versa.

As described above, the plurality of types of syringe adapters 300 and 400 can be provided corresponding to the syringes to be held, so that various syringes can be mounted on the injection head. In addition, since the functions of the lock mechanism to the injection head and of the lock mechanism of the syringe are common to syringe adapters 300 and 400, the syringe can be held tightly and can be mounted and demounted easily.

When the plurality of types of syringe adapters 300 and 400 are used in this manner, it is convenient to allow the injection head to identify easily which of syringe adapters 300 and 400 is mounted on the injection head, that is, which syringe is mounted on the injection head, and whether syringe adapter 300 or 400 is mounted. Thus, syringe adapters 300 and 400 preferably have adapter identifying members used to identify the types of syringe adapters 300 and 400.

In the following, a preferred embodiment of the adapter identifying member will be described with reference to FIG. 4 by taking syringe adapter 300 described first as an example.

Syringe adapter 300 is formed to be able to have up to four subjects to be detected 351a to 351d as the adapter identifying member. At least one of the number, the positions, the material, and the attachment method of the subjects to be detected 351a to 351d varies among the types of the syringe adapter. On the other hand, the injection head has at least one sensor for detecting the subjects to be detected 351a to 351d individually at the position opposite to the position where the subjects to be detected 351a to 351d can be attached in the state in which syringe adapter 300 is mounted. Which syringe adapter is mounted can be identified from the combination of the subjects to be detected 351a to 351d detected by the sensor. When any of the subjects to be detected 351a to 351d is not detected at any position, it is determined that no syringe adapter is mounted.

While the four subjects to be detected 351a to 351d can be provided in the present embodiment, the positions and the number of the subjects to be detected 351a to 351d are not limited particularly and can be set as appropriate in view of the type of the syringe adapter mounted on the injection head. For example when a small number of the types of syringe adapters are used, the number of subjects to be detected can be reduced accordingly. When a large number of the types of syringe adapters are used and cannot be dealt with by only the four subjects to be detected, the number of the subjects to be detected can be increased to more than four.

The adapter identifying member can be formed of various materials such as metal and plastic. The sensor for detecting the adapter identifying member can be realized by using an arbitrary sensor capable of detecting the adapter identifying member when syringe adapter 300 is appropriately mounted. Particularly, a proximity sensor for detecting the presence or absence and the position of an object in a non-contact manner can be preferably used. A representative proximity sensor uses magnetism as a detection medium to detect the presence or absence and the position of an object. The types of the magnetism detected by the proximity sensor include a direct-current static magnetic field and an alternating-current magnetic field.

When the proximity sensor using the direct-current magnetic field as the detection medium is used as the sensor, a magnet can be used as the adapter identifying member. As the proximity sensor capable of detecting the magnet, it is possible to use a semiconductor magnetic sensor such as a magnetic resistance element and a hall element, and a ferromagnetic sensor such as a flux gate type sensor, an MR (Magnet-Resistive) element, and an MI (Magneto-Impedance) element.

The proximity sensor for detecting the direct-current static magnetic field detects the polarity of the magnet. Thus, at least one magnet is placed as the adapter identifying member such that the orientation of the polarity is different for each type of the syringe adapter. Since the sensor detects the polarity of the magnet, it is possible to identify which syringe adapter is mounted from the combination of the detected polarities of the magnets. In this case, however, since the sensor detects the polarity of the magnet, correct detection cannot be performed if the magnet is attached with the polarity reversed due to errors in operation.

On the other hand, in the proximity sensor using the alternating-current magnetic field as the detection medium, metal can be used as the adapter identifying member, and no problem occurs from the errors in operation as described above. In addition, since the proximity sensor using the alternating-current magnetic field as the detection medium can detect the adapter identifying member at a distance smaller than that of the proximity sensor using the direct-current static magnetic field as the detection medium, the former can detect that the syringe adapter is mounted at the normal position more correctly. Consequently, in the present invention, the proximity sensor using the alternating-current magnetic field as the detection medium is preferably used as the sensor for detecting the adapter identifying member.

The proximity sensor using the alternating-current magnetic field as the detection medium has a coil and takes advantage of the fact that passing a certain alternating current through the coil by an alternating-current power source to provide the alternating-current magnetic field for the metal (adapter identifying member) produces eddy currents in the metal. The eddy currents produced in the metal cause a magnetic field to produce an induced voltage in the coil. As a result, when the metal is brought closer to the coil, the impedance of the coil which is the ratio of the voltage produced in the coil to the current passed through the coil is changed. The proximity sensor uses the change in the impedance to detect the metal.

The proximity sensor of this type is broadly classified into a single coil type in which one coil has the function as an excitation coil providing the alternating-current magnetic field for the adapter identifying member and the function as a detection coil detecting the eddy current magnetic field produced from the adapter identifying member and a multi coil type in which a plurality of coils are provided.

Examples of the type of the proximity sensor of the single coil type include a high-frequency oscillation type and a filter type. The proximity sensor of the high-frequency oscillation type incorporates a detection coil in part of an oscillation circuit and detects a change in the oscillation amplitude or the oscillation frequency in accordance with a change in impedance. The proximity sensor of the filter type incorporates a detection coil in part of an LC or LR filter circuit and uses the fact that the filter characteristics vary with a change in impedance of the detection coil.

Examples of the types of the proximity sensor of the multi coil type include a double coil type, a differential coil type, and a fork coil type.

The proximity sensor of the double coil type uses two coils of the same structure, in which one of them is brought closer to the adapter identifying member as the detection coil and the other is used as a reference coil and placed to avoid any influence of the adapter identifying member. When the two coils are excited under the same conditions and the difference in induced voltage is compared, it can be said that the difference in the induced voltage between them is produced by the approach of the adapter identifying member since the detection coil is affected by the approach of the adapter identifying member. A detection circuit is typically realized by constructing an impedance bridge with the two coils and exciting it through a fixed oscillator to detect the amplitude of the unbalanced voltage or the phase to the exciting current. Alternatively, the unbalanced voltage obtained from the bridge circuit is amplified and fed back to the excitation side of the bridge circuit to oscillate the circuit, and the resulting amplitude is detected.

In the proximity coil of the differential coil type, typically, detection coils are placed at symmetric positions on both sides of an excitation coil, and the terminals of the detection coils are connected in the series with the reverse polarities and are used as a detection output end. Since the excited magnetic flux produces the equal induced voltage in the detection coils, the induced voltage due to the excited magnetic field is cancelled, and only the induced voltage due to the magnetic flux produced by eddy currents can be taken out similarly to the double coil type. Then, similarly to the double coil type, it is only required to detect the amplitude or the phase of the output voltage at the terminal of the detection coil, or to amplitude the voltage at the terminal of the detection coil, feed it back to the excitation coil, and oscillate it.

In the proximity sensor of the fork coil type, the excitation coil and the detection coil are placed opposite to each other to make magnetic coupling, and the adapter identifying member is inserted between them to detect a change in the amplitude or the phase of the induced voltage produced in the detection coil.

Description has been made of various proximity sensors capable of detecting the metal in a non-contact manner by using the alternating-current magnetic field as the detection medium. Any of them can be used in the present invention. When the proximity sensor capable of detecting the metal is used, the adapter identifying member may be formed of metal entirely or partially.

The size and the shape of the adapter identifying member can be arbitrarily set as long as it does not interfere with the mounting of syringe adapter 300. Preferably, the adapter identifying member may be a ball plunger.

When the ball plunger is used as the adapter identifying member, the ball plunger is preferably attached such that part of a ball thereof is protruded from the surface of syringe adapter 300. On the other hand, adapter receiver 114*a* is preferably provided with a concave portion or a through hole for accommodating the proximity sensor at the position opposite to the ball plunger in the state in which syringe adapter 300 is mounted on adapter receiver 114*a* such that the ball of the ball plunger engages with the concave portion or the through hole. This allows the adapter detecting means to have an auxiliary lock function of syringe adapter 300 to adapter receiver 114a.

As described above, the proximity sensor can be placed within the concave portion or the through hole formed in adapter receiver 114a. In this case, the proximity sensor may be held through press fit into the concave portion or the through hole or may be held through screwing. The holding of the proximity sensor through screwing can facilitate the position adjustment of the proximity sensor within the concave portion or the through hole and the removal of the proximity sensor for replacing. The concave portion or the through hole may be filled with resin. This can increase resistance to water of the proximity sensor to reduce the possibility of a failure of the proximity sensor when the chemical liquid or the like is attached thereto.

While the syringe adapter has been described by using the representative embodiments as examples, the syringe adapter according to the present invention is not limited to the abovementioned embodiments, and the structure, the size and the like of the flange receiver and the flange lock mechanism can be changed as appropriate depending on the shape, the size and the like of the cylinder flange of the syringe to be held. For example, in the abovementioned embodiments, the cylinder flange of the syringe held by the syringe adapter has the two concave portions on the outer circumferential surface, and the flange lock mechanism is formed so as to fit to the concave portions. However, the number of the concave portions formed in the cylinder flange may be one, or three, four, or more. In this case, the position, the number and the like of the flange lock mechanism can be changed in accordance with the concave portion formed in the cylinder flange.

While the abovementioned embodiments have been described with the case in which the syringe adapter is applied to the chemical liquid injector, the syringe adapter of the present invention can be applied to a chemical liquid filler for filling a chemical liquid into an empty syringe.

DESCRIPTION OF REFERENCE NUMERALS

100 CHEMICAL LIQUID INJECTOR
110 INJECTION HEAD
114a ADAPTER RECEIVER
117 GUIDE GROOVE
118 ENGAGEMENT HOOK
200 SYRINGE
210 CYLINDER
211 CYLINDER FLANGE
212a CONCAVE PORTION (OF CYLINDER FLANGE)
220 PISTON
300, 400 SYRINGE ADAPTER
310 BASE MEMBER
312, 412 RIB
313, 327 ABUTTING SURFACE
320 FLANGE LOCK MEMBER
321 ARC-SHAPED PORTION (OF FLANGE LOCK MEMBER)
322, 422 ARM PORTION
323, 423 LOCK HOOK
324 ENGAGEMENT HOOK (OF FLANGE LOCK MEMBER)
325 GRIP PORTION
326, 426 INCLINED RIB
330, 430 FLANGE RECEIVING SURFACE
414 CYLINDER SUPPORT PORTION
415, 428 PLATE-SHAPED PORTION

The invention claimed is:

1. A syringe adapter for removably holding a syringe having a cylinder and a piston, the syringe adapter being mounted removably on an apparatus for operating the syringe, comprising:
 a flange receiver receiving a cylinder flange formed at a trailing end of the cylinder of the syringe to be held and matching a shape of the cylinder flange;
 a flange lock mechanism locking the cylinder flange by rotation of the syringe received in the flange receiver about an axis of the cylinder; and
 an adapter lock mechanism locking the syringe adapter to the apparatus so as not to release lock to the apparatus in a state in which the cylinder flange of the syringe is received in the flange receiver.

2. The syringe adapter according to claim 1, wherein the flange receiver has an arc-shaped portion having an inner circumferential surface with a radius of curvature substantially equal to a radius of curvature of an outer circumferential surface of the syringe flange, an arm portion extending from both ends of the arc-shaped portion and provided to be elastically displaceable with respect to the arc-shaped portion, and a grip portion formed on the arm portion,
 part of an inner circumferential surface of the grip portion is formed on an extension of an arc shape of the inner circumferential surface of the arc-shaped portion, and
 the adapter lock mechanism is provided for on an outer surface of the arm portion.

3. The syringe adapter according to claim 2, wherein the adapter lock mechanism has an engagement structure elastically engaging with an adapter receiving portion formed in the apparatus such that the syringe adapter is inserted therein.

4. The syringe adapter according to claim 3, further comprising a guide structure in inserting the syringe adapter in the adapter receiving portion.

5. The syringe adapter according to claim 4, wherein the guide structure is a rib formed to extend in a direction in which the syringe adapter is inserted.

6. The syringe adapter according to claim 5, wherein the adapter receiving portion has a guide groove for guiding the rib, and
 an inclined rib located on an extension of the rib and applying a force for raising the syringe adapter from the adapter receiving portion in cooperation with a side wall of the guide groove in association with elastic displacement of the arm portion is formed on the arm portion.

7. The syringe adapter according to claim 3, further comprising an adapter identifying member used to identify a type of the syringe adapter by the apparatus when the syringe adapter is inserted into the adapter receiving portion.

8. The syringe adapter according to claim 7, wherein the adapter identifying member is at least one magnet.

9. The syringe adapter according to claim 2, further comprising a stopper structure limiting an elastic displacement amount of the arm portion.

10. The syringe adapter according to claim 1, further comprising a cylinder support portion supporting the cylinder of the syringe.

11. An apparatus on which the syringe adapter according to claim 1 is removably mountable, comprising:
 an adapter receiving portion into which the syringe adapter is inserted; and
 an engagement structure provided for the adapter receiving portion and locking the syringe adapter in cooperation with an adapter lock mechanism of the syringe adapter.

* * * * *